US006836362B2

(12) United States Patent
Potyrailo et al.

(10) Patent No.: US 6,836,362 B2
(45) Date of Patent: Dec. 28, 2004

(54) METHOD FOR THE RAPID DETERMINATION OF THE OPTICAL QUALITY OF COMBINATORIAL LIBRARIES

(75) Inventors: Radislav Alexandrovich Potyrailo, Niskayuna, NY (US); Michael Jarlath Brennan, Burnt Hills, NY (US); Daniel Robert Olson, Voorheesville, NY (US)

(73) Assignee: General Electric Company, Niskayuna, NY (US)

( * ) Notice: Subject to any disclaimer, the term of this patent is extended or adjusted under 35 U.S.C. 154(b) by 358 days.

(21) Appl. No.: 09/854,718

(22) Filed: May 14, 2001

(65) Prior Publication Data

US 2003/0038941 A1 Feb. 27, 2003

(51) Int. Cl.$^7$ .......................... G01N 11/04; G01N 21/55
(52) U.S. Cl. ...................... 359/445; 356/364; 356/365; 356/367; 356/337; 356/338; 73/54.05; 73/54.07; 73/54.02; 73/54.32; 73/54.34
(58) Field of Search ................... 356/337, 338, 356/343, 445–448, 339.1, 364–367, 429, 212, 73, 243, 406, 318, 237; 205/122; 422/99; 435/288.5; 514/396; 526/65; 702/30, 39; 73/54.02, 54.04, 54.05, 54.07, 54.32, 54.34; 250/459.1, 559.2; 428/262, 304.4, 44.7

(56) References Cited

U.S. PATENT DOCUMENTS

| | | | |
|---|---|---|---|
| 3,999,864 A | 12/1976 | Mutter | 356/212 |
| 4,168,249 A | 9/1979 | Meyer | 260/16 |
| 4,255,308 A | 3/1981 | Brasen | 260/29.6 |
| 4,285,597 A | 8/1981 | Lamprecht et al. | 356/446 |
| 4,651,011 A | 3/1987 | Ors et al. | 250/459 |
| 4,687,338 A | 8/1987 | Task et al. | 356/446 |
| 4,715,717 A | 12/1987 | Evans | 356/429 |
| 4,885,254 A | 12/1989 | Sung | 436/85 |
| 4,886,355 A | 12/1989 | Keane | 356/73 |
| 4,978,731 A | 12/1990 | Melancon et al. | 528/15 |
| 4,996,076 A | 2/1991 | Nakaya et al. | 427/38 |
| 5,037,763 A | 8/1991 | Petisce | 436/172 |

(List continued on next page.)

FOREIGN PATENT DOCUMENTS

WO       WO 00/13004       3/2000

OTHER PUBLICATIONS

*Photoluminescence Methods In Polymer Science*, SW Beavan et al., Adv. Photochem, 11 pp. 207–303, 1979.
*Fluorescence Methods in Polymer Science*, Yasunori Nishijima, Polymer Sci.: Part C, No. 31, pp 353–373, 1970.
*Analysis of Polymer Systems By Luminescence Spectroscopy*, LS Bark et al., len, Editors. UK. (1982) Applied Science Publishers LTD, London, pp. 79–102, 1982.

(List continued on next page.)

*Primary Examiner*—John R. Lee
*Assistant Examiner*—David A. Vanore
(74) *Attorney, Agent, or Firm*—Andrew J. Caruso; Patrick K. Patnode

(57) ABSTRACT

This invention provides methodology for the measurement of both low and high levels of scattered radiation produced by decorative and barrier coatings and plastics. Measurements of low levels are especially important for coatings used in automotive applications. The method is based on the illumination of the sample with radiation and collection of only the portion of the radiation scattered from the coating before, during and after the testing step and relating the optical signal from the tested portion of the sample material to the untested portion of the material and/or a standard. Through the practice of the invention, a large number of coating samples, as in an array, may be analyzed for their optical quality, principally haze, either after coating and curing, and/or after subjection of such coatings samples to elongation stresses, and/or abrasion testing, solvent exposure, hydrolytic stability testing, and temperature exposure.

44 Claims, 11 Drawing Sheets

U.S. PATENT DOCUMENTS

| | | | |
|---|---|---|---|
| 5,098,750 A | 3/1992 | Ueno et al. | 428/304.4 |
| 5,118,559 A | 6/1992 | DeVoe et al. | 428/262 |
| 5,155,558 A | 10/1992 | Tannenbaum et al. | 356/446 |
| 5,198,869 A | 3/1993 | Monteverde et al. | 356/243 |
| 5,218,417 A | 6/1993 | Gay et al. | 356/300 |
| 5,244,636 A | 9/1993 | Walt et al. | 422/82.07 |
| 5,310,604 A | 5/1994 | Melancon et al. | 428/447 |
| 5,384,079 A | 1/1995 | Bur et al. | 264/21 |
| 5,416,594 A | 5/1995 | Gross et al. | 356/237 |
| 5,464,986 A | 11/1995 | Boettcher et al. | 250/459.1 |
| 5,483,338 A | 1/1996 | Wachter et al. | 356/318 |
| 5,550,632 A | 8/1996 | Harata | 356/446 |
| 5,552,890 A | 9/1996 | Nanna et al. | 356/369 |
| 5,556,663 A | 9/1996 | Chang et al. | 427/8 |
| 5,598,005 A | 1/1997 | Wang et al. | 250/459 |
| 5,606,171 A | 2/1997 | Neckers et al. | 250/459 |
| H1655 H | 6/1997 | Task | 356/446 |
| 5,644,141 A | 7/1997 | Hooker et al. | 250/559.22 |
| 5,680,220 A | 10/1997 | Delignieres et al. | 356/406 |
| 5,707,587 A | 1/1998 | Blanchard et al. | 422/82.08 |
| 5,712,709 A | 1/1998 | Task et al. | 356/432 |
| 5,714,762 A | 2/1998 | Li et al. | 250/559.2 |
| 5,717,217 A | 2/1998 | Neckers et al. | 250/459.1 |
| 5,742,386 A | 4/1998 | Nose et al. | 356/237 |
| 5,788,374 A | 8/1998 | Bur et al. | 374/161 |
| 5,817,732 A | 10/1998 | Asahina et al. | 528/45 |
| 5,829,804 A | 11/1998 | Saeki et al. | 293/120 |
| 5,867,807 A | 2/1999 | Yamada et al. | 702/30 |
| 6,018,396 A | 1/2000 | Rapaport et al. | 356/446 |
| 6,031,620 A | 2/2000 | Typpo | 356/445 |
| H1843 H | 3/2000 | Bur et al. | 250/458 |
| 6,088,104 A | 7/2000 | Peterson | 356/371 |
| 6,151,123 A * | 11/2000 | Nielsen | 356/445 |
| 6,157,449 A | 12/2000 | Hajduk | 356/367 |
| 6,769,292 B2 * | 8/2004 | Mansky et al. | 73/54.05 |

OTHER PUBLICATIONS

*Luminescence Applications In Commercial Polymers*, NS Allen et al., Chemistry and Industry, London, 23, pp. 907–913, Dec. 2, 1978.

*The Use of Luminescence Spectroscopy in Aiding the Identification of Commercial Polymers*, NS Allen et al., Analyst, vol. 101, London, pp. 260–264, Apr. 1976.

*Transducer–Based Approached for Parallel Binding Assays in HTS*, Andreas Brecht et al., Journal of Biomolecular Screening, vol. 1, No. 4, pp. 191–201, 1996.

*Optical Sensor Arrays Based On Micotiterplate Dimensions*, Gunter Gauglitz, Mikrochim. Acta, 131, pp. 91–97, 1999.

*Some Applications of Fluorimetry To Synthetic Polymer Studies*, Herbert Morawetz, Science, vol. 203, No. 4379, pp. 405–410, Feb. 2, 1979.

*High–Conversion Polymerization Fluorescence Probes. 1. Polymerization of Methyl Methacrylate*, Rafik O. Loutfy, Macromolecules, 14, pp. 270–275, 1981.

*Fluorescence Probes for Polymerization Reactions: Bulk Polymerization of Styrene, n–Butyl Methacrylate, Eethyl Methacrylate, and Ethyl Aacrylate*, Rafik O. Loutfy, Journal of Polymer Science, Polymer Physics Edition, vol. 20, pp. 825–835, 1982.

*Optical Fibers Make Sense of Chemicals*, Jane A. Ferguson et al., Photonics Spectra, 14, pp. 108–114, Mqrch 1997.

*Generating Sensor Diversity Through Combinatorial Polymer Synthesis*, Todd A. Dickinson, Anal. Chem. 69, pp. 3413–3418, 1997.

*Standard Test Method for Resistance of Transparent Plastics to Surface Abrasion*, ASTM D 1044–94, 1994.

*Standard Test Method for Haze and Luminous Transmittance of Transparent Plastics*, ASTM D 1003–97, 1997.

*Ultraviolet and Visible Molecular Absorption Spectorphotometry*, Spectrochemical Analysis, James D. Ingle, Jr. et al., Prentice Hall, Englewood Cliffs, NJ, Chapter 13, pp. 352–403, 1988.

*Molecular Luminescence Spectrometry*, Spectrochemical Analysis, James D. Ingle, Jr. et al., Prentice Hall, Englewood Cliffs, NJ, Chapter 15, pp. 438–493, 1988.

*Molecular Scattering Methods*, Spectrochemical Analysis James D. Ingle, Jr. et al., Prentice Hall, Englewood Cliffs, NJ, Chapter 16, pp. 494–524, 1988.

*Standard Test Methods for Abrasion Resistance of Organic Coatings by Falling Abrasive*, ASTM D 968–93.

*Standard Test Method for Abrasion Resistance of Organic Coatings by the Taber Abraser*, ASTM D 4060–95.

*Standard Test Method for Abrasion Resistance of Transparent Plastics and Coatings Using the Oscillating Sand Method*, ASTM F 735–94.

*Standard Test Methods for Resistance of Plastic Materials to Abrasion*, ASTM D 1242–95a.

*Paint and Coating Testing Manual*, Joseph V. Koleske, Editor, Fourteenth Edition of the Gardner–Sward Handbook, ASMT Manual Series: MNL 17, ASTM Publication Code No. (PCN) 28–017095–14, pp. 513–525.

*Standard Practice for Testing Water Resistance of Coatings Using Water Immersion*, ASTM D 870–92.

*Standard Test Method for Peel Adhesion of Pressure–Sensitive Tape at 180° Angle*, ASTM D 3330/D 3330M–96, pp. 372–375.

*Standard Test Methods for Measuring Adhesion by Tape Test*, ASTM D 3359–92a, pp. 447–450.

*Standard Test Method for Adhesion of Organic Coatings by Scrape Adhesion*, ASTM D 2197–98, pp. 216–218.

*Standard Test Method for Pull–Off Strength of Coatings Using Portable Adhesion Testers*, ASTM D 4541–95, pp. 327–333.

*Standard Test Method for Tensile Properties of Plastics*, ASTM D 638–98, pp. 45–57.

*Standard Test Method for Tensile Properties of Organic Coating*, ASTM D 2370–92, pp. 251–254.

*Standard Test Methods for Mandrel Bend Test of Attached Organic Coatings*, ASTM D 522–93a, pp. 29–32.

*Microscopic Dynamics of the Glass Transition Investigated By Time–Resolved Fluorescence Measurements of Doped Chromophores*, Jing Yong Ye et al., The American Physical Society, Physical Review B, vol. 56, No. 9, pp. 5286–5296, Sep. 1, 1997.

*Determination of the Molecular Mobility and the Free Volume of Thin Polymeric Films With Fluorescence Probes*, Dirk Anwand et al., Makromol. Chem., 192, pp 1981–1991, 1981.

*Photochemistry of Ketone Polymers, XI. Phosphorescence As A Probe of Subgroup Motion in Polymers at Low Temperatures*, AC Somersall et al., vol. 7, No. 2, pp. 233–244.

* cited by examiner

US 6,836,362 B2

METHOD FOR THE RAPID DETERMINATION OF THE OPTICAL QUALITY OF COMBINATORIAL LIBRARIES

STATEMENT REGARDING FEDERALLY SPONSORED RESEARCH

The U.S. Government may have certain rights in this invention pursuant to National Institutes of Standards and Technology (NIST) Contract No. 70NANB9H3038.

BACKGROUND OF THE INVENTION

The present invention relates to methods and systems for the rapid measurement of the scattering properties of decorative and barrier coatings and plastics arrays, which in turn are indicators of the overall integrity of the coating or plastic material.

Applications of decorative and barrier coatings include finishing the exteriors of automobile and truck bodies, appliances, electronic parts, and other high-quality products. In the combinatorial discovery of coating materials for applications such as decorative and barrier coatings, the rapid evaluation of the optical quality of the coating itself is of considerable importance. Optical quality of coatings such as haze and light, or electromagnetic radiation, scattering is affected by several factors. These factors include internal haze levels during coating deposition and curing, scattering defects due to poor abrasion resistance, and crack formation during elongation, hydrolytic stability tests, and exposure to solvents. Thus, the optical quality of the coating is directly related to the coating condition and the overall integrity of the film. There is a direct correlation between the amount of scattered radiation and the quality of the coating.

A typical method for such measurements is haze determination. In this method, a relatively large area of the coating (about 1 cm$^2$) is measured to provide values for the transmitted and diffused (scattered) radiation. Haze is calculated as the ratio of the diffuse transmitted radiation to the total transmitted radiation. This measurement method has several shortcomings that limit its applicability for the high throughput applications such as those for the screening of combinatorial libraries. These drawbacks include difficulties in obtaining reliable measurements of haze values of less than 0.5%, the need to have a relatively large coating area for measurements, impossibility in the determination of the presence of a transparent coating on the substrate, difficulties in the rapid measurement of multiple samples on non-flat substrates, impossibility of measurements of haze on opaque substrates, and difficulties in measurement automation. As a result, reliable evaluation of optical parameters of multiple small-scale transparent thin coatings presents an analytical measurement challenge. Thus, the need exists to provide a means for performing high throughput measurements.

BRIEF SUMMARY OF THE INVENTION

This invention provides methodology for the measurement of both low and high levels of scattered radiation produced by decorative and barrier coatings. Measurements of low levels of scattered radiation are especially important for coatings such as those used in automotive applications. The method is based on the illumination of a coating sample with an electromagnetic radiation source and collection of only a portion of the radiation scattered from the coating. Good correlation has been found between the data obtained via the practice of this invention and such data obtained via more cumbersome and inherently limited methodology such as that set forth in ASTM D 1003, and other tests. Through the practice of the invention, a large number of coating samples, as in an array, may be analyzed for their optical quality, i.e., principally haze, either after coating and curing, and/or after subjecting such coatings samples to elongation stresses and/or abrasion and hydrolytic stability testing. An advantage of this invention is that when analyzing an array, the substrate is used as a reference for comparison of the optical quality of the substrate to that of the coating sample. In such an array, the uncoated substrate areas between the individual members of the coating array or library may be utilized as internal standards. A further advantage is the capability to analyze the standards and various abraded coating regions to determine the relative performance of a member of the combinatorial array or library.

DETAILED DESCRIPTION OF INVENTION

The present invention provides a system for the optical interrogation of combinatorial arrays comprising a combinatorial array having a surface with a plurality of predefined regions, the plurality of predefined regions comprising one or more samples and reference regions, a radiation source operable to expose each of the plurality of predefined regions of the combinatorial array to incident radiation of at least one selected wavelength and intensity, a detector operable to measure the resultant radiation for each of the plurality of predefined regions of the combinatorial array, and a computer to functionally control the operation of the system and determine the relative performance of each of the plurality of predefined regions of the combinatorial array.

The present invention also provides a method for the measurement of haze of at least one sample, including exposing the at least one sample to radiation of at least one predetermined wavelength, collecting less than all of the radiation interacting with the at least one sample, and calculating percentage haze of the at least one sample by measuring the amount of scattered radiation collected from a coating region relative to the amount of radiation collected from a reference region.

In the practice of the present invention, transmission haze and reflection haze are measured on coatings and substrates of different natures. In one embodiment, the sample is a coated sample. In an alternative embodiment, the sample is a plastic film or plaque.

Figure 1:
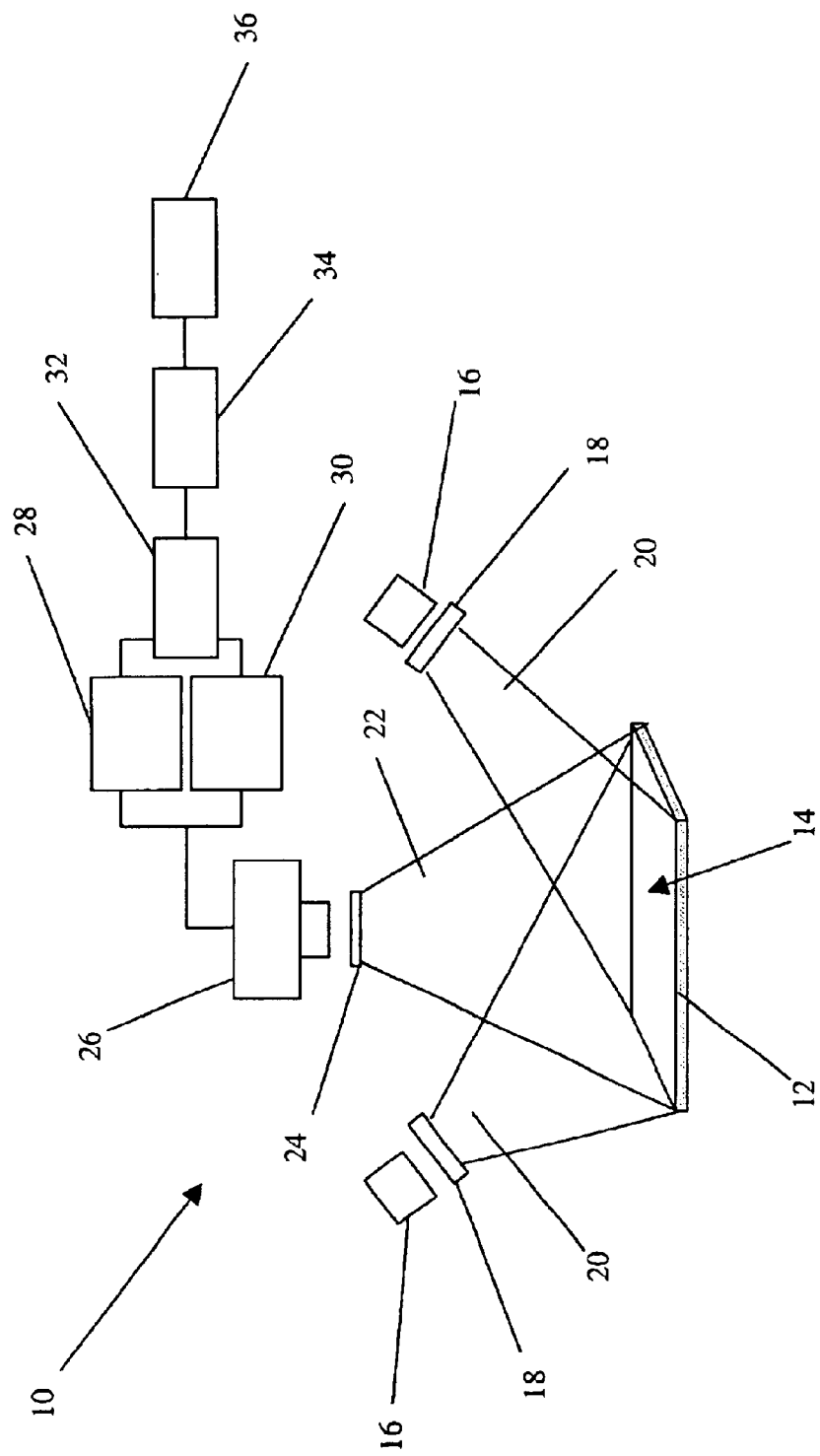
FIG. 1 is a schematic diagram of an optical interrogation system for screening combinatorial arrays of coatings and plastics.
Figure 2:
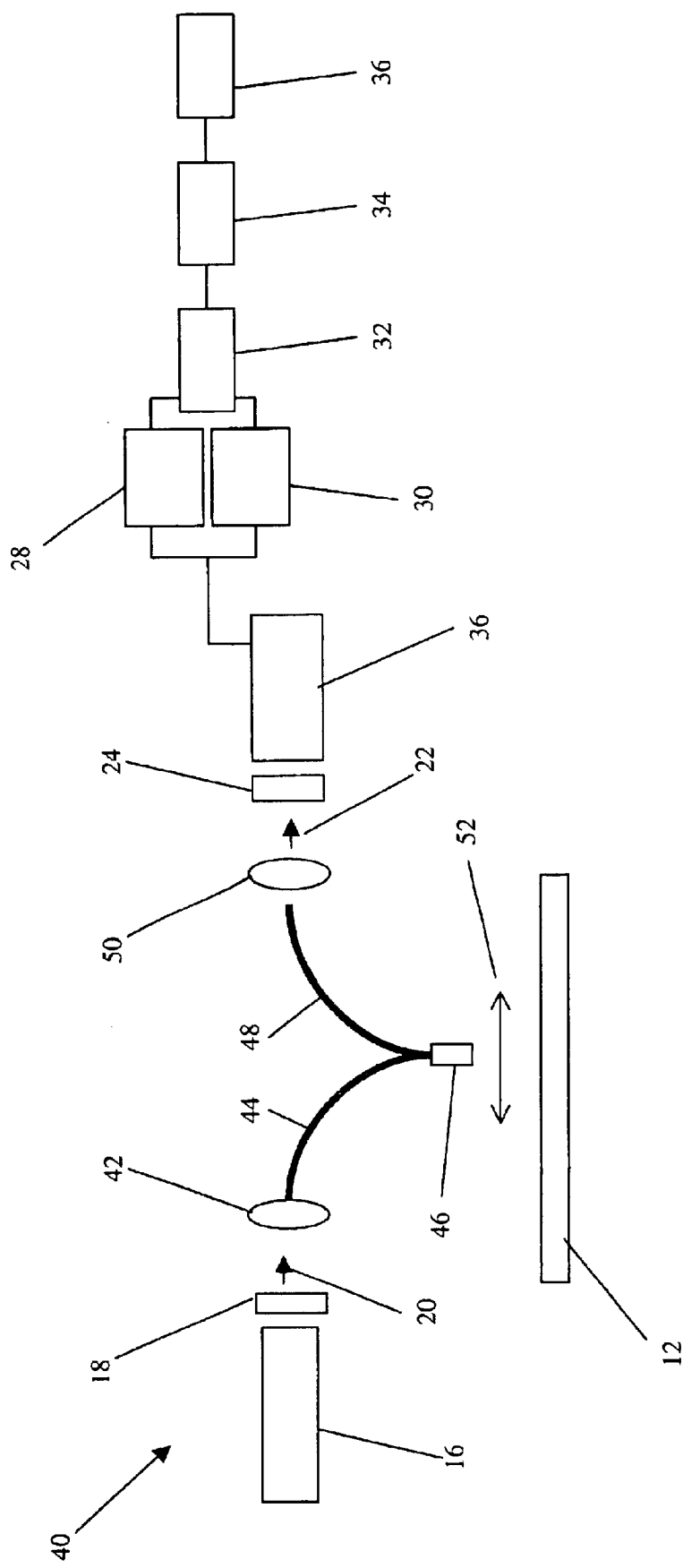
FIG. 2 is a schematic diagram of a one probe set up of an optical interrogation system for screening combinatorial arrays of coatings and plastics.

Referring to FIGS. 1 and 2, in one embodiment, a system 10 for the optical interrogation of combinatorial arrays of coatings and substrates includes a combinatorial array 12 having a surface 14 with a plurality of predefined regions, an electromagnetic radiation source 16 for transmitting incident radiation 20 onto the surface 14, and a detector 26 for measuring the resultant radiation 22 in the form of elastically scattered radiation, reflected and/or transmitted radiation, and luminescence.

Incident radiation 20 of a selected wavelength and intensity is transmitted from the radiation source 16 to each of the plurality of predefined regions of the combinatorial array 12 via an excitation wavelength selection element 18. The resultant radiation 22 transmitted through, reflected from, or emitted by each material/member associated with the plurality of predefined regions of the combinatorial array 12 passes through the emission wavelength selection element 24 and imaging detector 26, where the spectral data is collected in an initial screen 28 before the testing step. The data is further collected at intermediate screen 30 after the testing step. Data from the initial 28 and intermediate 30 screens is mathematically processed to generate results of mathematical image processing 32. These results are displayed as distribution maps of resultant radiation 34 and unacceptable and/or acceptable amounts of resultant radiation in transparent coatings are highlighted in the screen 36.

The optical interrogation system 10 may include a computer in communication with all of the components of the system 10. The computer may control the position of the combinatorial array 12 within the system 10. The computer may also control the operation of the radiation source 18, the wavelength selection elements 18, 24, the imaging detector 26, and the screens 28, 30.

In an alternative embodiment of the present invention, FIG. 2 depicts a serial analysis system 40. In this illustration, one or more transparent coatings and the substrate 12 is irradiated with a radiation source 16 via an excitation wavelength selection element 18, focusing lens 42, and an optical fiber 44. The optical fiber 44 delivers radiation to the probe 46. The excitation radiation 20 is selected as desired based on the optical characteristics of the coatings (absorption, reflection, luminescence spectra, etc.), spectral response of the radiation source 16, detector 26, and other opto-electronic components. The emission radiation 22 is captured by a probe 46 and is directed into the optical fiber 48, passes through the lens 50 and emission wavelength selection element 24 and is detected with a detector 26. A plurality of coatings is evaluated by positioning probe 46 over different coatings in the array 12. Positioning 52 can be achieved by moving the probe 46 or/and coatings on the array 12. The spectral data from coatings of interest is collected in an initial screen 28 before the testing step. The data is further collected at an intermediate screen 30 after the testing step. Data from the initial 28 and intermediate 30 screens is mathematically processed to generate results of mathematical processing 32. These results are displayed as an array 34 of distribution of scattered light in each individual coating or a portion of the coating and unacceptable and/or acceptable identified levels of resultant radiation in transparent coatings are highlighted in the array 36.

The methodology of the present invention may be used to analyze plastic samples and coatings samples for intrinsic haze, i.e., the haze present in a given sample due to incompatibility of components, curing methods, etc., as well as haze induced in such samples following physical exposure to elongation or torsional stresses, hydrolytic stability testing with either hot or cold water, exposure to temperature, exposure to at least one solvent for a predetermined period of time, exposure to at least one fluid for a predetermined period of time, and after being subjected to abrasion, which can be analyzed using traditional Taber testing in conjunction with the present method. The abrasion testing of the samples may be conducted in a similar fashion as the following methods: ASTM D968 Standard Test Methods for Abrasion Resistance of Organic Coatings by Falling Abrasive, ASTM D4060 Standard Test Method for Abrasion Resistance of Organic Coatings by the Taber Abraser, ASTM F735 Standard Test Method for Abrasion Resistance of Transparent Plastics and Coatings Using the Oscillating Sand Method, ASTM D1044 Standard Test Method for Resistance of Transparent Plastics to Surface Abrasion, and ASTM D1242 Test Methods for Resistance of Plastic Materials to Abrasion.

The present invention can also be used as a method for the rapid determination of haze in large numbers of coating samples or samples of plastic films or plaques. Thus, in a further embodiment, the present invention provides a method for the analysis of an array of coated samples or plastics, which includes exposing an array to radiation of at least one predetermined wavelength, collecting less than all of the radiation interacting with the array, and calculating percentage haze based on at least one predetermined reference.

Figure 3:
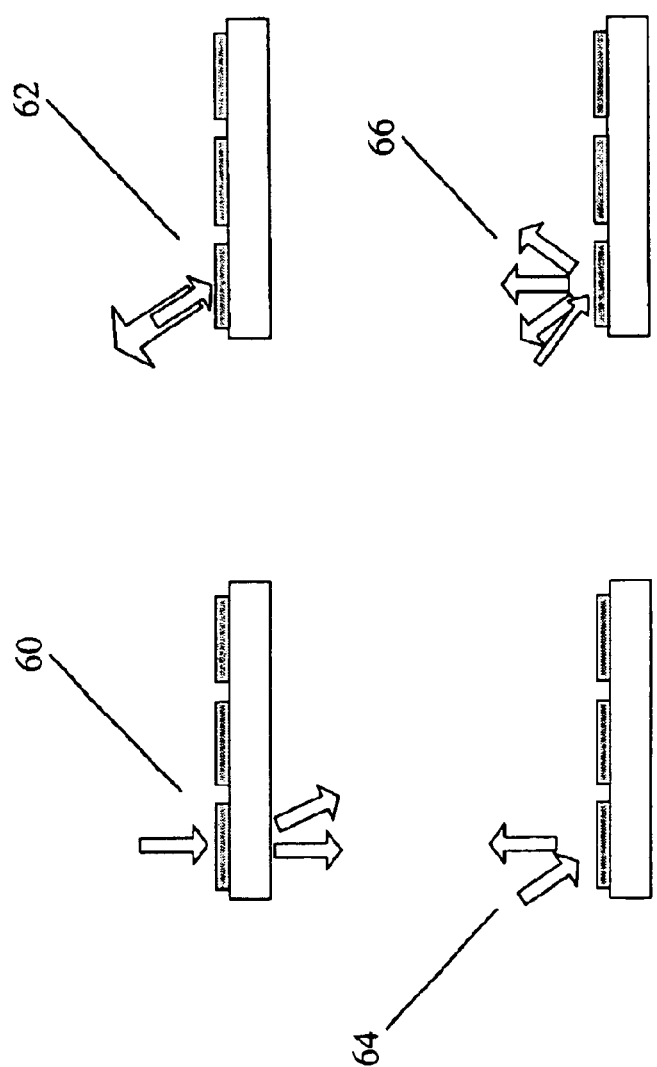
FIG. 3 is a schematic diagram of the spectral signal acquisition modes of the optical interrogation system of FIGS. 1 and 2.

Measurements of transmitted radiation (transmission haze) as depicted in FIG. 3, provide information about the optical quality of highly scattering coatings and plastics. In this configuration, the radiation losses due to scattering reduce the amount of radiation transmitted through 60 the coating and substrate 12 and captured by a photo-detector. The smallest haze values reliably measured using this configuration are more than 0.5% haze.

Measurements of diffusively reflected radiation (reflection haze) as illustrated in FIG. 3 (62, 64, 66) provide information about the optical quality of scattering coatings and plastics when the coating and substrate are opaque or haze levels are small enough and are unable to be measured with the configuration shown in 60. The smallest haze values reliably measured using configurations illustrated in 62, 64, and 66 are less than 0.5% haze. Attractive features of these methods include high sensitivity through measurements of small signal changes on top of a small background, and, a simple intensity vs. haze relationship.

Illumination conditions illustrated in FIG. 3 (62, 64, and 66) are selected to collect only the diffusively reflected portion of radiation interacting with the surface. Typical angles between the direction of the incident and collected beams are in the range from about 0 degrees to about 180 degrees. Typical angles between the direction of the incident beam and the normal to the surface are in the range from about 0 degrees to about 90 degrees. Configuration 62 depicts the irradiation of a sample with radiation of one wavelength and the collection of radiation of the same wavelength at a 360 degree angle to the emitted radiation. Configurations 64 and 66 depict the irradiation of a sample with radiation of a given wavelength and the collection of radiation at a different collection angle 64 and at multiple collection angles 66.

An experimental setup used for the demonstration of this invention includes a white light (radiation) source (SLM Instruments, Inc.) and a CCD camera (Roper Scientific) with associated image acquisition software and automated image analysis software (National Instruments).

The amount of radiation that must be collected to be able to generate reliable data depends on the required dynamic range of measurements and the parameters of the optical system.

Figure 4:
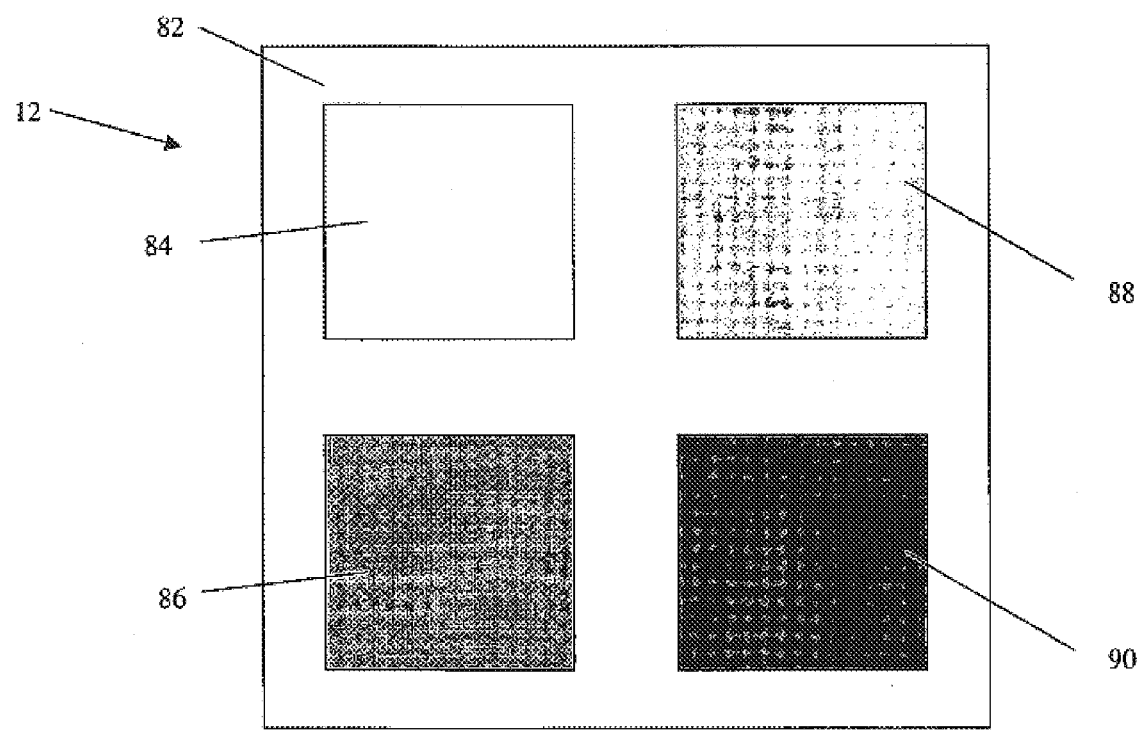
FIG. 4 depicts an array of coating materials deposited on a single substrate after an abrasion performance test of the entire regions of coatings and substrate.
Figure 5:
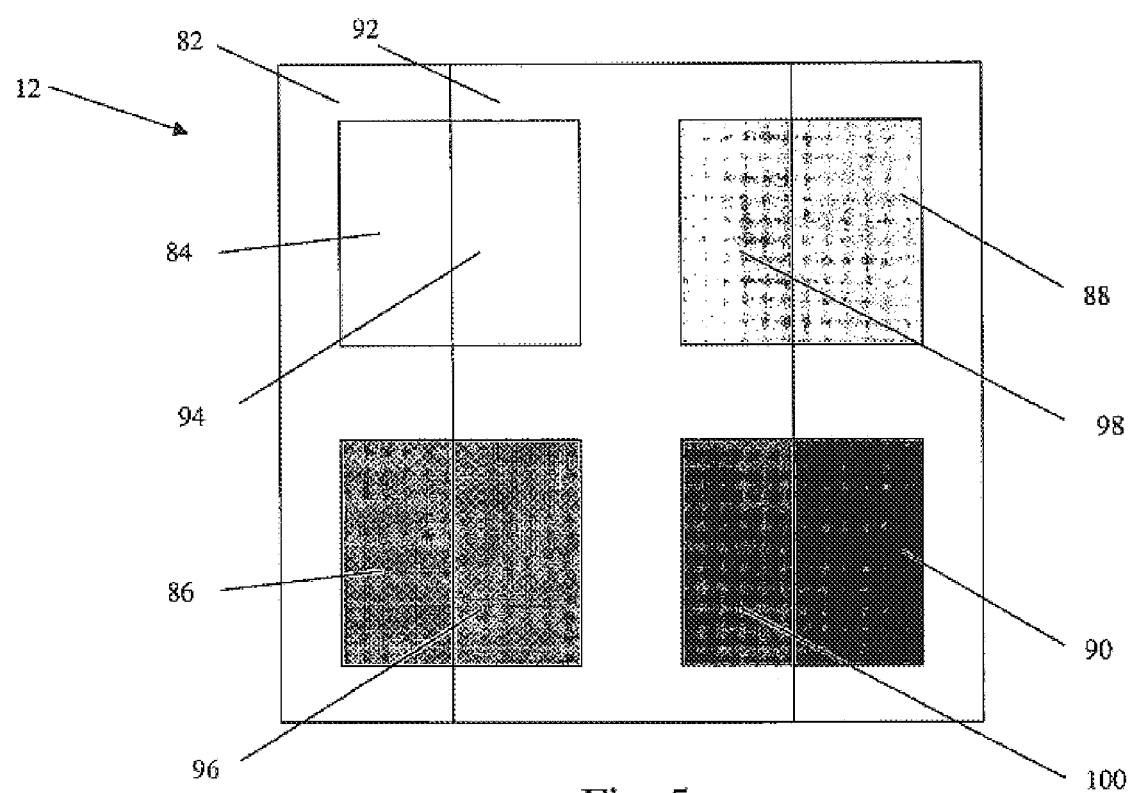
FIG. 5 depicts an array of coating materials deposited on a single substrate after an abrasion performance test of certain regions of coatings and substrate.

Referring to FIGS. 4 and 5, the combinatorial array 12 comprises any library or array of discrete or continuous materials that may be studied using optical interrogation methods. Preferably, the combinatorial array 12 includes a coated substrate, a plurality of samples of polymeric material arranged in an array, a plurality of wells arranged in an array where each well contains a polymeric material, or a plurality of wells arranged in an array where each well contains a sensor comprising a chemically sensitive material. The substrate may comprise a plastic, glass, metal, or composite material. The substrate may comprise a transparent material or an opaque material. The substrate may be concave or convex. The coating may also be comprised of a transparent material or an opaque material. For example, the combinatorial array 12 may include a substrate coated with a thin film decorative, barrier, mar-resistant, weatherable, anticorrosive, adhesive/release, or electric conductive coating. These coatings may be organic or inorganic. The coatings may, for example, vary in composition, thickness, curing characteristics across the array, substrate characteristics such as morphology, surface energy, or any other parameters of the coatings and the substrate to form a combinatorial coating library. Areas or predefined regions of the coatings may also be selected as samples or members of the library or array, separated by a mask or other means, and subjected to varying degrees of adhesion/abrasion, elongation/torsion, solvent/radiation exposure, and any other test needed to evaluate the performance of the materials.

Referring to FIG. 4, coating materials 84, 86, 88, 90 are deposited onto the substrate 82. The screening of adhesion/abrasion, elongation/torsion, solvent/radiation, and any other resistance parameter of the coating materials is performed using either serial or parallel tools. The adhesion/abrasion, elongation/torsion, solvent/radiation, and any other resistance parameter of the coating materials is measured as the amount of resultant radiation collected from a coating region relative to the amount of radiation collected from a substrate 82 region.

The method allows for the measurement of resultant radiation from both a reference region (substrate) 82 and coating region 84, 86, 88, 90 in a single instrumental setup without repositioning of either the reference 82 or coating regions 84, 86, 88, 90 relative to each other.

Also, the method allows for the measurement of resultant radiation from both a reference region (substrate) 82 and coating region 84, 86, 88, 90 almost simultaneously. This approach improves the precision of these determinations because it compensates for any instability of the radiation source 16 and detector 26. Also, this method allows the real time analysis of resultant radiation during the performance testing.

In addition, this measurement method compensates for any non-reproducibility of the incidence angle (FIG. 3; 60, 62, 64, 66) of the probe (FIG. 2; 46) radiation 20 with respect to the substrate 82 with a deposited coating. Such misalignment does not change the relative signal (or signal ratio) of the amount of resultant radiation (FIG. 1; 22) collected from a coating region relative to the amount of radiation collected from a substrate 82 region. The amount of the non-reproducibility of the incidence angle of the probe 46 radiation is in the range from about −10 to about +10 degrees relative to a present angle. This insensitivity to the non-reproducibility of the incidence angle of the probe 46 radiation with respect to the substrate 82 with the deposited coating permits the use of curved substrates with deposited coatings.

Referring to FIG. 5, coating materials 84, 86, 88, 90 are deposited onto the substrate 82. An abrasion or any other type of a performance test is performed on certain regions of the coatings and the substrate 82. These regions are either regions 84, 86, 88, 90 (coatings) and the substrate 82, or regions 94, 96, 98, 100 (coatings) and the substrate 92.

In addition to features provided by the abrasion testing and measurement of the coatings and the substrate depicted in FIG. 4, the approach presented in FIG. 5 has an additional feature. It provides simultaneous information about an initial value of scattered radiation from unabraded regions of the substrate and the coatings. This information is useful in evaluating the change in the amount of scattered radiation before and after the abrasion test.

Figure 6:
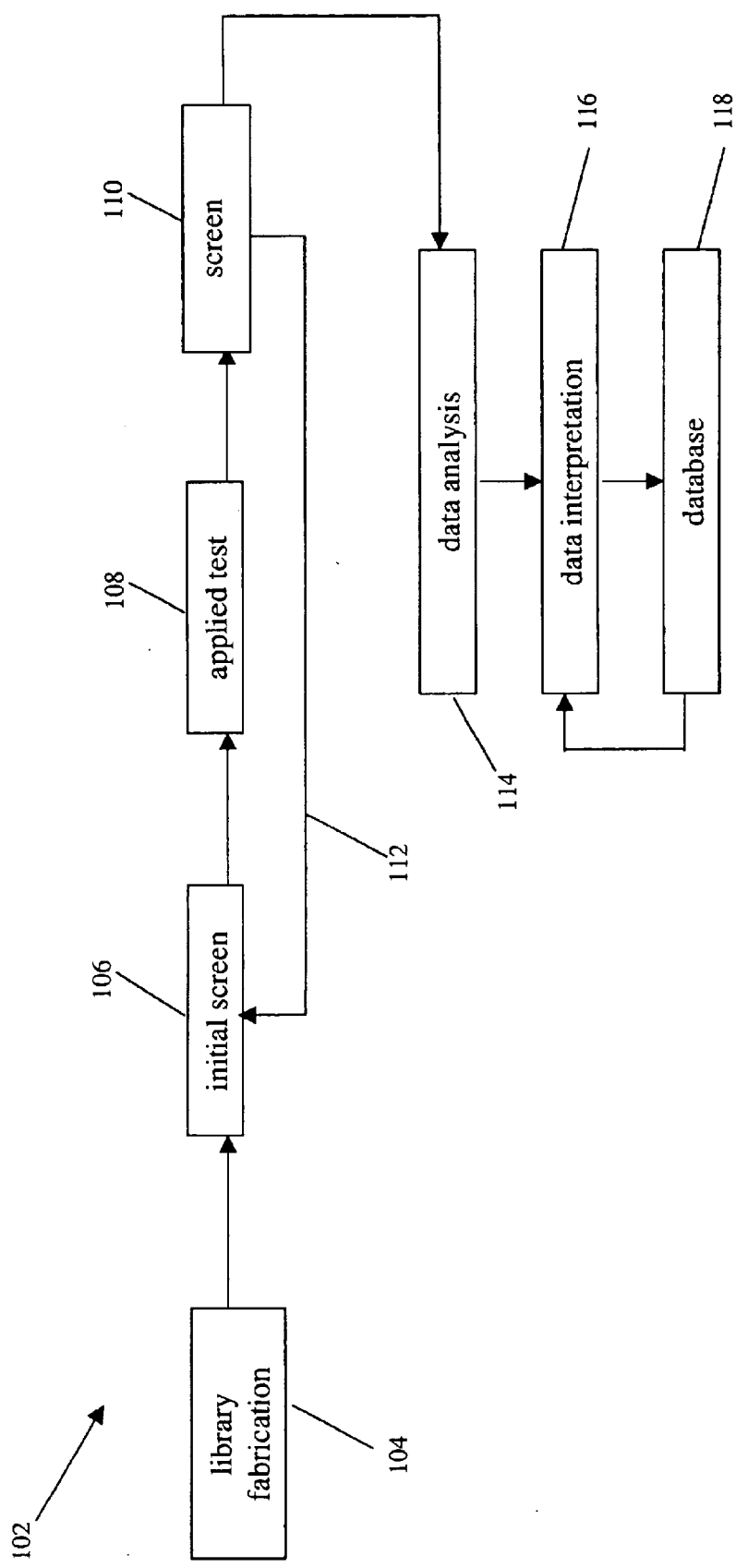
FIG. 6 is a functional block diagram of an optical interrogation method for screening combinatorial arrays of coatings and plastics.

FIG. 6 is a block diagram of a method 102 for the optical interrogation of combinatorial arrays of coatings and plastics where the coating sample or library to be analyzed is fabricated 104 and run through an initial screen 106. The testing is then applied 108 and the screening is conducted a second time 110. The test can then be reapplied 112 via an iterative process or the data can be analyzed 114 and interpreted 116 over time. This methodology also contemplates an iterative process for the data interpretation 116 and the development of a database 118 of spectral data indicating optical quality of characteristics, e.g., haze, for a given coating on a given substrate.

This methodology also permits the analysis of a coating array during the performance testing. This, in situ analysis, further increases the throughput of screening.

Figure 7:
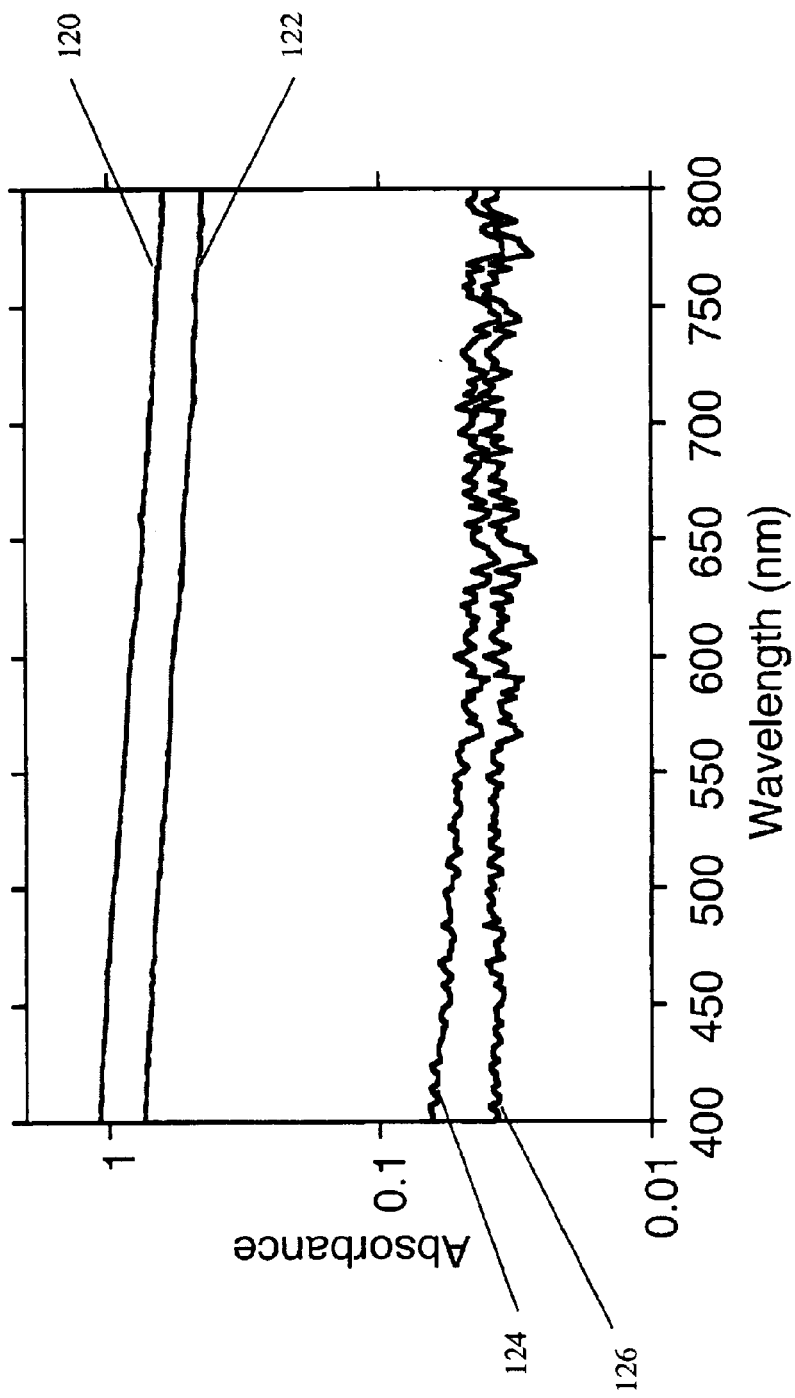
FIG. 7 is a graph illustrating the variation of intensity of scattered radiation from a coating obtained using the spectroscopic analysis of scattered radiation in different thin films.

FIG. 7 illustrates the variation of intensity of transmitted radiation in different thin films. Curves 120 and 122 illustrate thin films with high haze values (i.e., highly scattering films), curve 124 illustrates a thin film with low haze values (i.e., a weakly scattering film), and curve 126 illustrates a substrate with no coating. Techniques developed in this invention are more sensitive than conventional absorption measurements. FIG. 7 compares absorption spectra of materials with high (curves 120 and 122) and low haze values (curve 124). Clearly, a material with a high haze scatters a significant amount of transmitted radiation as indicated by the elevated absorbance level. This absorbance decreases as the wavelength of probe radiation increases, in accordance with scattering theories. Similar wavelength-dependent absorption is observed for a low-haze material. However, a negligible absorbance level in the latter material over the visible range of the spectrum makes measurements of transmitted radiation problematic for the reliable quantification of low haze values below 1% haze.

In the practice of the present invention, any source of electromagnetic radiation may be utilized, but it is preferred that a source such as those shown in Table 1 having a wavelength range of about 200 nm to about 2,500 nm be utilized. In the above method, it is preferred that a portion, i.e., about 0.01% to about 99.99% of the scattered radiation is collected using an integrating sphere.

TABLE 1

Radiation Sources Useful for Determination of Optical Quality of Materials

| Source | Spectral range of emission (nm) |
|---|---|
| Continuous wave sources: | |
| Hollow cathode | |
| Hinteregger lamp | 20–600 |
| Xenon arc lamp | 200–1000 |
| Mercury arc lamp | 250–600 |
| Deuterium lamp | 180–420 |
| Tungsten lamp | 320–2500 |
| Light emitting diodes | different diodes cover range from 370 to 1500 |
| Diode lasers | different diode lasers cover range from about 400 to 1500 |
| Argon ion laser | several lines over 350–514 |
| Helium-neon laser | several lines over 543–633 |
| Krypton laser | several lines over 530–676 |
| Pulsed sources: | |
| Excimer lasers | 157, 193, 248, 308, 351 |
| Nitrogen laser | 337 |
| Nd:YAG laser | fundamental - 1064, frequency doubled - 532, tripled - 355, quadrupled - 266 |
| Ti:Sapphire laser | 720–1000, frequency doubled 360 to 500 |
| Dye lasers | 360–990 frequency doubled 235 to 345 |

Unlike other methods for the measurement of scattered radiation used to evaluate the quality of decorative or barrier coatings, the measurements of scattered radiation can be performed at a wavelength that is different from the wavelength of the radiation source. These measurements can be performed when a coating exhibits an inherent luminescence under a certain range of excitation wavelengths or the coating substrate itself exhibits inherent luminescence. Alternatively, the coating composition may be doped with a small amount of a luminescent compound or the substrate can be doped with a small amount of a luminescent compound, i.e., about 1 fM to about 1 mM. Luminescence properties such as luminescence intensity and others of the luminescent compound are not affected by the microenvironment, e.g. coating and/or substrate formulation, polarity, glass transition temperature, etc. Luminescence can be strongly influenced by the microenvironment which includes environmentally sensitive dye— dye interactions, microviscosity of the environment, temperature, solvent, and environment polarity. Thus, in a further preferred embodiment, there is provided the method of the present invention, wherein the at least one sample exhibits luminescence at a wavelength different from the wavelength of the predetermined wavelength. In a further preferred embodiment, there is provided the method of the present invention wherein the at least one sample is comprised of a substrate having a coating thereon, and wherein the substrate exhibits luminescence at a wavelength different from the wavelength of the predetermined wavelength.

The following is a partial list of commercially available, suitable luminescent dyes.

5-Amino-9-diethyliminobenzo(a)phenoxazonium Perchlorate

7-Amino-4-methylcarbostyryl

7-Amino-4-methylcoumarin

7-Amino-4-trifluoromethylcoumarin 3-(2'-Benzimidazolyl)-7-N,N-diethylaminocoumarin 3-(2'-Benzothiazolyl)-7-diethylaminocoumarin 2-(4-Biphenylyl)-5-(4-t-butylphenyl)-1,3,4-oxadiazole 2-(4-Biphenylyl)-5-phenyl-1,3,4-oxadiazole 2-(4-Biphenyl)-6-phenylbenzoxazole-1,3

2,5-Bis-(4-biphenylyl)-1,3,4-oxadiazole 2,5-Bis-(4-biphenylyl)-oxazole 4,4'-Bis-(2-butyloctyloxy)-p-quaterphenyl p-Bis(o-methylstyryl)-benzene 5,9-Diaminobenzo(a)phenoxazonium Perchlorate 4-Dicyanomethylene-2-methyl-6-(p-dimethylaminostyryl)-4H-pyran 1,1'-Diethyl-2,2'-carbocyanine Iodide 1,1'-Diethyl-4,4'-carbocyanine Iodide 3,3'-Diethyl-4,4',5,5'-dibenzothiatricarbocyanine Iodide 1,1'-Diethyl-4,4'-dicarbocyanine Iodide 1,1'-Diethyl-2,2'-dicarbocyanine Iodide 3,3'-Diethyl-9,11-neopentylenethiatricarbocyanine Iodide 1,3'-Diethyl-4,2'-quinolyloxacarbocyanine Iodide 1,3'-Diethyl-4,2'-quinolylthiacarbocyanine Iodide 3-Diethylamino-7-diethyliminophenoxazonium Perchlorate 7-Diethylamino-4-methylcoumarin 7-Diethylamino-4-trifluoromethylcoumarin 7-Diethylaminocoumarin 3,3'-Diethyloxadicarbocyanine Iodide 3,3'-Diethylthiacarbocyanine Iodide 3,3'-Diethylthiadicarbocyanine Iodide 3,3'-Diethylthiatricarbocyanine Iodide 4,6-Dimethyl-7-ethylaminocoumarin 2,2'-Dimethyl-p-quaterphenyl 2,2-Dimethyl-p-terphenyl 7-Dimethylamino-1-methyl-4-methoxy-8-azaquinolone-2

7-Dimethylamino-4-methylquinolone-2

7-Dimethyl amino-4-trifluoromethylcoumarin 2-(4-(4-Dimethylaminophenyl)-1,3-butadienyl)-3-ethylbenzothiazolium Perchlorate 2-(6-(p-Dimethylaminophenyl)-2,4-neopentylene-1,3,5-hexatrienyl)-3-methylbenzothiazolium Perchlorate 2-(4-(p-Dimethylaminophenyl)-1,3-butadienyl)-1,3,3-trimethyl-3H-indolium Perchlorate 3,3'-Dimethyloxatricarbocyanine Iodide 2,5-Diphenylfuran 2,5-Diphenyloxazole 4,4'-Diphenylstilbene 1-Ethyl-4-(4-(p-Dimethylaminophenyl)-1,3-butadienyl)-pyridinium Perchlorate 1-Ethyl-2-(4-(p-Dimethylaminophenyl)-1,3-butadienyl)-pyridinium Perchlorate 1-Ethyl-4-(4-(p-Dimethylaminophenyl)-1,3-butadienyl)-quinolium Perchlorate 3-Ethylamino-7-ethylimino-2,8-dimethylphenoxazonium Perchlorate 9-Ethylamino-5-ethylamino-10-methyl-5H-benzo(a)phenoxazonium Perchlorate 7-Ethylamino-6-methyl-4-trifluoromethylcoumarin 7-Ethylamino-4-trifluoromethylcoumarin 1,1',3,3,3,3'-Hexamethyl-4,4',5,5'-dibenzo-2,2'-indotricarboccyanine Iodide 1,1',3,3,3',3'-Hexamethylindodicarbocyanine Iodide 1,1',3,3,3',3-Hexamethylindotricarbocyanine Iodide 2-Methyl-5-t-butyl-p-quaterphenyl N-Methyl-4-trifluoromethylpiperidino-<3,2-g>coumarin 3-(2'-N-Methylbenzimidazolyl)-7-N,N-diethylaminocoumarin 2-(1-Naphthyl)-5-phenyloxazole 2,2'-p-Phenylen-bis(5-phenyloxazole)

3,5,3"",5""-Tetra-t-butyl-p-sexiphenyl 3,5,3"",5""-Tetra-t-butyl-p-quinquephenyl 2,3,5,6-1H,4H-Tetrahydro-9-acetylquinolizino-<9,9a,1-gh>coumarin 2,3,5,6-1H,4H-Tetrahydro-9-carboethoxyquinolizino-<9,9a,1-gh>coumarin 2,3,5,6-1H,4H-Tetrahydro-8-methylquinolizino-<9,9a,1-gh>coumarin 2,3,5,6-1H,4H-Tetrahydro-9-(3-pyridyl)-quinolizino-<9,9a,1-gh>coumarin 2,3,5,6-1H,4H-Tetrahydro-8-trifluoromethylquinolizino-<9,9a,1-gh>coumarin 2,3,5,6-1H,4H-Tetrahydroquinolizino-<9,9a,1-gh>coumarin 3,3',2",3'''-Tetramethyl-p-quaterphenyl 2,5,2"",5""-Tetramethyl-p-quinquephenyl P-terphenyl P-quaterphenyl Nile Red Rhodamine 700

Oxazine 750

Rhodamine 800

IR 125

IR 144

IR 140

IR 132

IR 26

IR5

Diphenylhexatriene

Diphenylbutadiene

Tetraphenylbutadiene

Naphthalene

Anthracene 9,10-diphenylanthracene

Pyrene

Chrysene

Rubrene

Coronene

Phenanthrene

Fluorene

Aluminum phthalocyanine and

Platinum octaethylporphyrin.

In the practice of the invention, organic and inorganic calorimetric and luminescent particles that are insoluble can be doped into the substrate. These particles can be pigments, metal and semiconductor nanoparticles, nanotubes, nanowires, etc. These materials provide luminescence which can have higher long-term stability and are less responsive to photobleaching. Optical properties such as luminescence intensity, color, and others of the particles are not affected by the microenvironment, e.g. coating and/or substrate formulation, polarity, glass transition temperature, etc.

WORKING EXAMPLES

The following are working examples utilizing the systems and methods described above. These examples are to be considered as illustrative of the principles of the present invention, and should not be considered as limiting the scope of the invention in any manner.

1. Parallel Analysis of Regions of Coatings after an Abrasion Test.

For the experimental validation of the disclosed method, a 12×4-cm sheet of polycarbonate was flow coated with a coating derived from a mixture of methyltrimethoxysilane, colloidal silica, and n-butylalcohol. The coating was dried in air for about 10 min and cured at 130° C. for 30 minutes. A mask with 11×11 openings was positioned on top of the coating. Circular openings in the mask were 3-mm in diameter with 5-mm spacing between centers. Seven rows of the coating exposed through the mask were subjected to a stream of 50-$\mu$m $Al_2O_3$ particles at a constant pressure and flow applied with a pencil blaster. The array was automatically advanced under the operating pencil blaster with a speed of 5.5 in/min using a single-axis translation stage. The angle of the pencil blaster was normal to the coating surface. To induce various levels of coating abrasion, the distance to the coating surface was changed from 1 to 4 inches in 0.5-in. increments. Analysis of the scattered radiation was performed on seven abraded rows and referenced to the regions of coating protected from abrasion by the mask.

Spatially resolved mapping of coating abrasion can be performed using a setup which included a white light source (450-W Xe arc lamp, SLM Instruments, Inc., Urbana, Ill., Model FP-024), a monochromator for selection of the illumination wavelength (SLM Instruments, Inc., Model FP-092), and a CCD camera (Roper Scientific, Trenton, N.J., Model TE/CCD 1100 PF/UV) with associated image acquisition software (Roper Scientific) and automated image analysis software (National Instruments). The illumination wavelength is selected at 520 nm using the monochromator and the radiation is directed to the sample. Scattered light from the abraded and unabraded regions of the coatings is collected with the camera with an integration time of about 0.02–1 sec.

Figure 8:
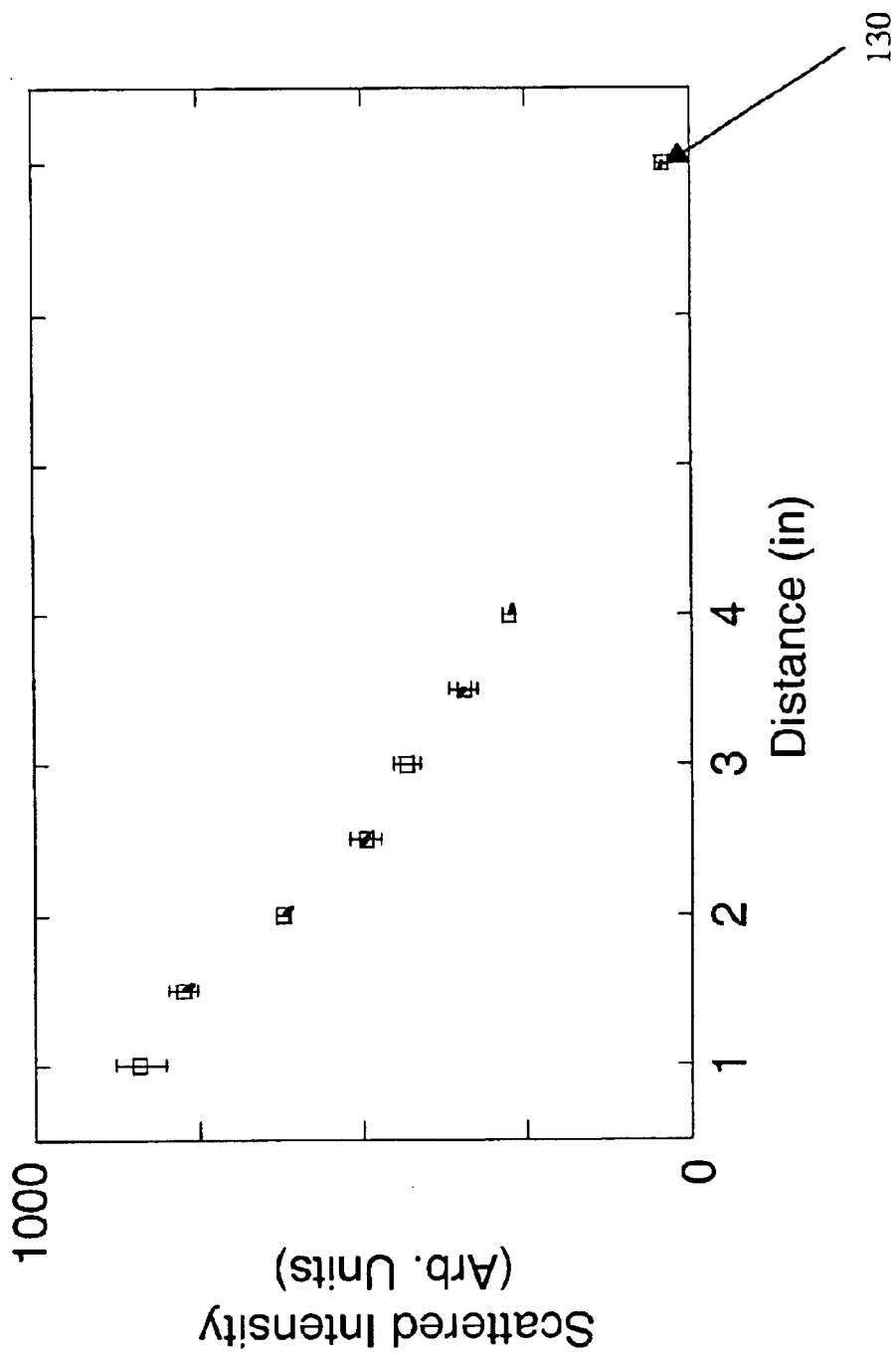
FIG. 8 is a plot illustrating variation of intensity of scattered radiation from a coating as a function of coating/sand blaster distance obtained from the spatially resolved map of distribution of scattered radiation in an array of abraded coating regions.

FIG. 8 demonstrates the variation of intensity of resultant radiation from the coating as a function of coating/sand blaster distance. The error bars are one standard deviation from the mean of 11 measurements (a whole row of coatings). The sand blasting increases coating abrasion upon decreasing the distance between the pencil blaster and coating. However, at short distances, there is less increase in the scattered radiation intensity due to the removal of the coating down to the substrate. When the sand blaster is far enough away from the coating sample, the coating sample remains unabraded 130.

2. Serial Analysis of Regions of Coatings After an Abrasion Test.

For the experimental validation of the disclosed method for abrasion resistance and adhesion, a 12×4-cm sheet of polycarbonate was flow coated with a coating derived from a mixture of methyltrimethoxysilane, colloidal silica, and n-butyl alcohol. The coating was dried in air for about 10 min and cured at 130° C. for 30 minutes. A mask with 11×11 openings was positioned on top of the coating. Circular openings in the mask were 3-mm in diameter with a 5-mm spacing between the centers. Seven rows of the coating exposed through the mask were subjected to a stream of 50-$\mu$m $Al_2O_3$ particles at a constant pressure and flow applied with a pencil blaster. The array was automatically advanced under the operating pencil blaster with a speed of 5.5 in/min using a single-axis translation stage. The angle of the pencil blaster was normal to the coating surface. To induce various levels of coating abrasion, the distance to the coating surface was changed from 1 to 4 inches in 0.5-in. increments. The analysis of scattered radiation was performed on seven abraded rows and referenced to the regions of coating protected from abrasion by the mask.

Determinations of scattered light were performed on a setup which included a white light source (450-W Xe arc lamp, SLM Instruments, Inc., Urbana, Ill., Model FP-024), a monochromator for selection of the illumination wavelength (SLM Instruments, Inc., Model FP-092), and a portable spectrometer (Ocean Optics, Inc., Dunedin, Fla., Model ST2000). The spectrometer was equipped with a 200-$\mu$m slit, 600-grooves/mm grating blazed at 400 nm and covering the spectral range from 250 to 800 nm with efficiency greater than 30%, and a linear CCD-array detector. Light from the monochromator was focused into one of the arms of a "six-around-one" bifurcated fiber-optic reflection probe (Ocean Optics, Inc., Model R400-7-UV/VIS). Light from the coating was collected when the common end of the fiber-optic probe was positioned near the coating at a 45° angle to the normal to the surface. The second arm of the probe was coupled to the spectrometer. For measurements of scattered radiation the illumination wavelength was set to 510 nm.

Figure 9:
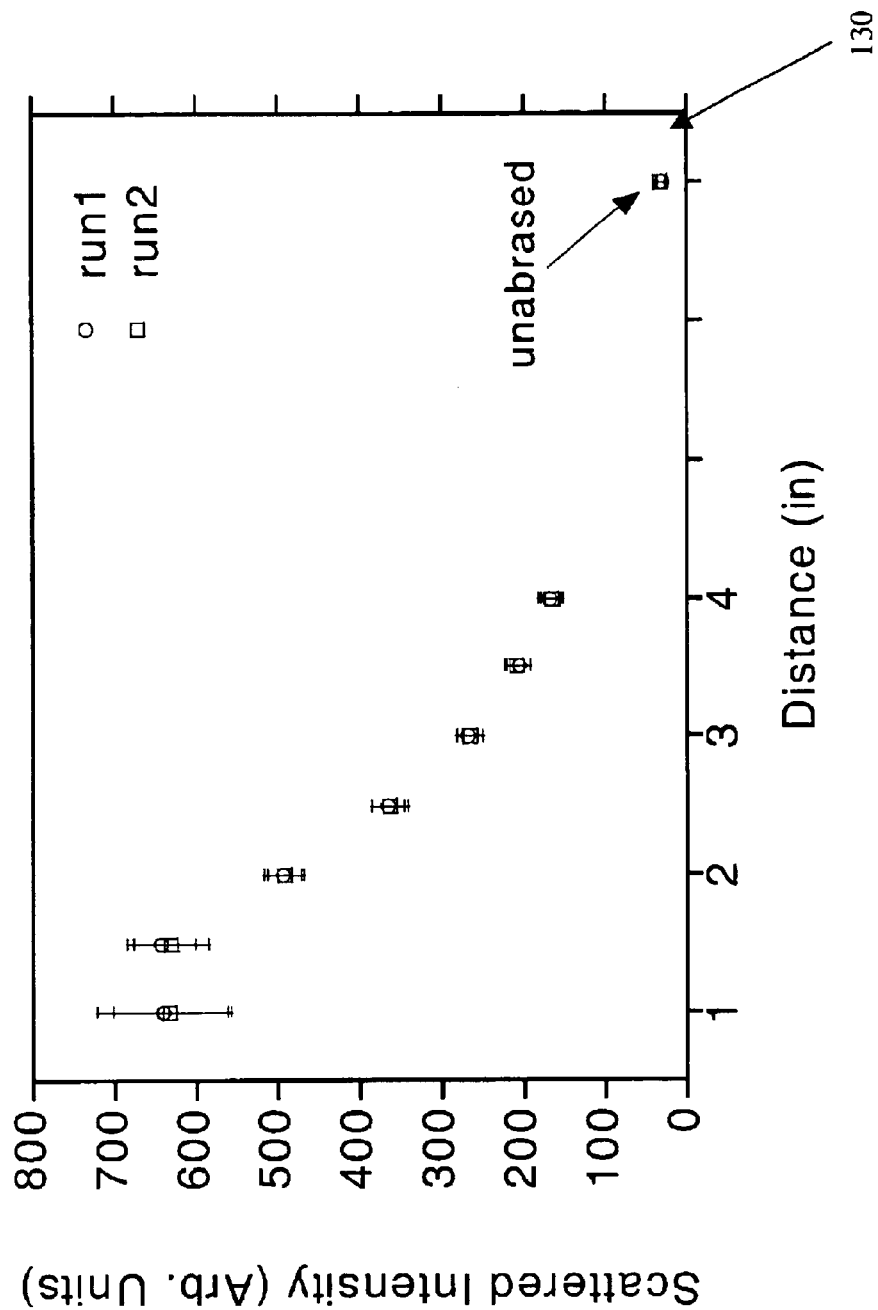
FIG. 9 is a plot illustrating variation of intensity of scattered radiation from a coating as a function of coating/sand blaster distance obtained using serial analysis method of measurement of distribution of scattered radiation in an array of abraded coating regions.

FIG. 9 demonstrates the variation of intensity of scattered radiation from the coating as a function of coating/sand blaster distance. The error bars are one standard deviation from the mean of 11 measurements (a whole row of coatings). Two measurements (runs 1 and 2) over the same coating regions performed at different times and with about 0.5–1 mm offsets from each other show no differences indicating even abrasion of material at distances 2–4 in. between the pencil blaster and coating. The sand blasting increases coating abrasion upon decreasing the distance between the pencil blaster and coating. However, at short distances, there is less increase in the scattered radiation intensity due to the removal of coating down to the substrate. When the sand blaster is at a great enough distance from the coating sample, the coating sample remains unabraded 130.

The intensities of scattered radiation from coating regions upon different abrasion conditions are summarized in Table 2. Measurements of scattered radiation were performed after the correction against the scattered radiation values from unabraded regions of the coatings.

TABLE 2

Intensities of scattered radiation from coatings after different abrasion conditions

| Sample Number | Coating/sand blaster distance (in) | Corrected Scatter signal (arbitrary units) |
|---|---|---|
| 1 | Unabraded | 0.0000 |
| 2 | 4 | 134.22 |
| 3 | 3.5 | 176.33 |
| 4 | 3 | 234.37 |
| 5 | 2.5 | 330.98 |
| 6 | 2 | 460.02 |
| 7 | 1.5 | 599.09 |
| 8 | 1 | 599.99 |

3. Serial Analysis of Regions of Coating Libraries.

A 12×9-cm sheet of polycarbonate was coated with an array of coatings derived from eight liquid coating formulations. They were deposited using a liquid handling robot (Packard Instrument Co., Model Multiprobe Ill., Meriden, Conn.). The coating deposition was performed using 8-microliter volumes of coating formulations in methoxypropanol at concentration of 20% solids, pipetting them into separate spatial locations provided with a 48-element mask, and UV curing of the film. The 48-element coating library contained eight different coating formulations with six replicates each. Table 3 depicts the formulations used for the coating array. Coating formulations 1–5 were from UCB Chemical Corp., North Augusta, S.C. Coating formulations 6–8 were from Sartomer Co., West Chester, Pa.

TABLE 3

Coating formulations

| Coating formulation number | Coating formulation name | Description |
|---|---|---|
| 1 | Ebecryl 1290 acrylated urethane | acrylated aliphatic urethane oligomer hexa-functional |
| 2 | Ebecryl 8804 aliphatic urethane | diacrylate - acrylated aliphatic urethane oligomer |
| 3 | Ebecryl 140 acrylate ester | tetraacrylate monomer |
| 4 | DPGDA acrylate ester | dipropylene glycol diacrylate monomer |
| 5 | Ebecryl 8301 acrylated urethane | acrylated aliphatic urethane oligomer |
| 6 | SR 238 | 1,6-hexanediol diacrylate |
| 7 | CD-401 | cyclohexane dimethanol dimethacrylate - di-functional cycloaliphatic methacrylate monomer. |
| 8 | SR 399 | dipentaerythritol pentaacrylate |

Figure 10:
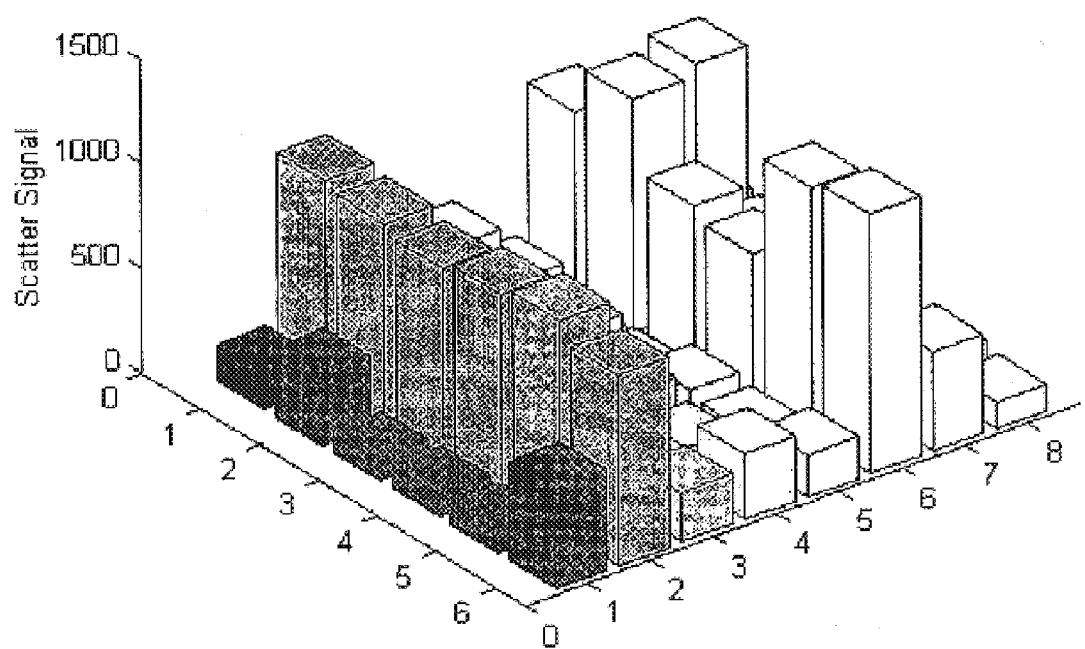
FIG. 10 is a plot of the high throughput serial analysis of a coating library after abrasion testing as set forth in Table 3 below.

The coating library was analyzed before and after the oscillating sand abrasion test using the measurement system described in Example 2. Results of the serial analysis of the coating library are presented in FIG. 10 and Table 4.

TABLE 4

Results of the serial analysis of coating library

| replicate number | Column (formulation) number | | | | | | | |
|---|---|---|---|---|---|---|---|---|
| | 1 | 2 | 3 | 4 | 5 | 6 | 7 | 8 |
| 1 | 172.93 | 981.7 | 312.2 | 445.23 | 172.02 | 878.07 | 632.12 | 202.87 |
| 2 | 334.49 | 948.36 | 257.66 | 252.2 | 99.69 | 1104.6 | 1166.6 | 207.06 |
| 3 | 115.12 | 909.27 | 447.71 | 262.22 | 73.886 | 767.15 | 491.88 | 96.726 |
| 4 | 112.24 | 953.92 | 354.04 | 253.97 | 168.36 | 705.53 | 432.32 | 108.97 |
| 5 | 106.75 | 998.82 | 173.34 | 176.18 | 134.51 | 1188.3 | 391.58 | 162.35 |
| 6 | 474.27 | 907.5 | 237.59 | 315.88 | 199.26 | 1237.2 | 472.78 | 125.22 |

4. Serial Analysis of Regions of Coatings After an Abrasion Test Using Luminescence.

A 12×4-cm sheet of polycarbonate was flow coated with a coating derived from a mixture of methyltrimethoxysilane, colloidal silica, and n-butyl alcohol doped with a luminophore (Lumogen F Red300, BASF). Such luminophore is typically used to induce decorative and other features in polymers and coatings. Spectral properties of the luminophore are not affected by its microenvironment. The coating was dried in air for about 10 min and cured at 130° C. for 30 minutes. The concentration of the luminophore in the cured coating was about 250 ppm. A mask with 11×11 openings was positioned on top of the coating. Circular openings in the mask were 3-mm in diameter with a 5-mm spacing between centers. Seven rows of the coating exposed through the mask were subjected to a stream of 50-$\mu$m $Al_2O_3$ particles at a constant pressure and flow applied with a pencil blaster. The array was automatically advanced under the operating pencil blaster with a speed of 5.5 in/min using a single-axis translation stage. The angle of the pencil blaster was normal to the coating surface. To induce various levels of coating abrasion, the distance to the coating surface was changed from 1 to 4 inches in 0.5-in. increments. An analysis of luminescence was performed on seven abraded rows and regions of the coating were protected from abrasion by the mask and referenced to the unabraded regions. Spectral determinations of luminescence were performed on a setup as described in example 2.

Figure 11:
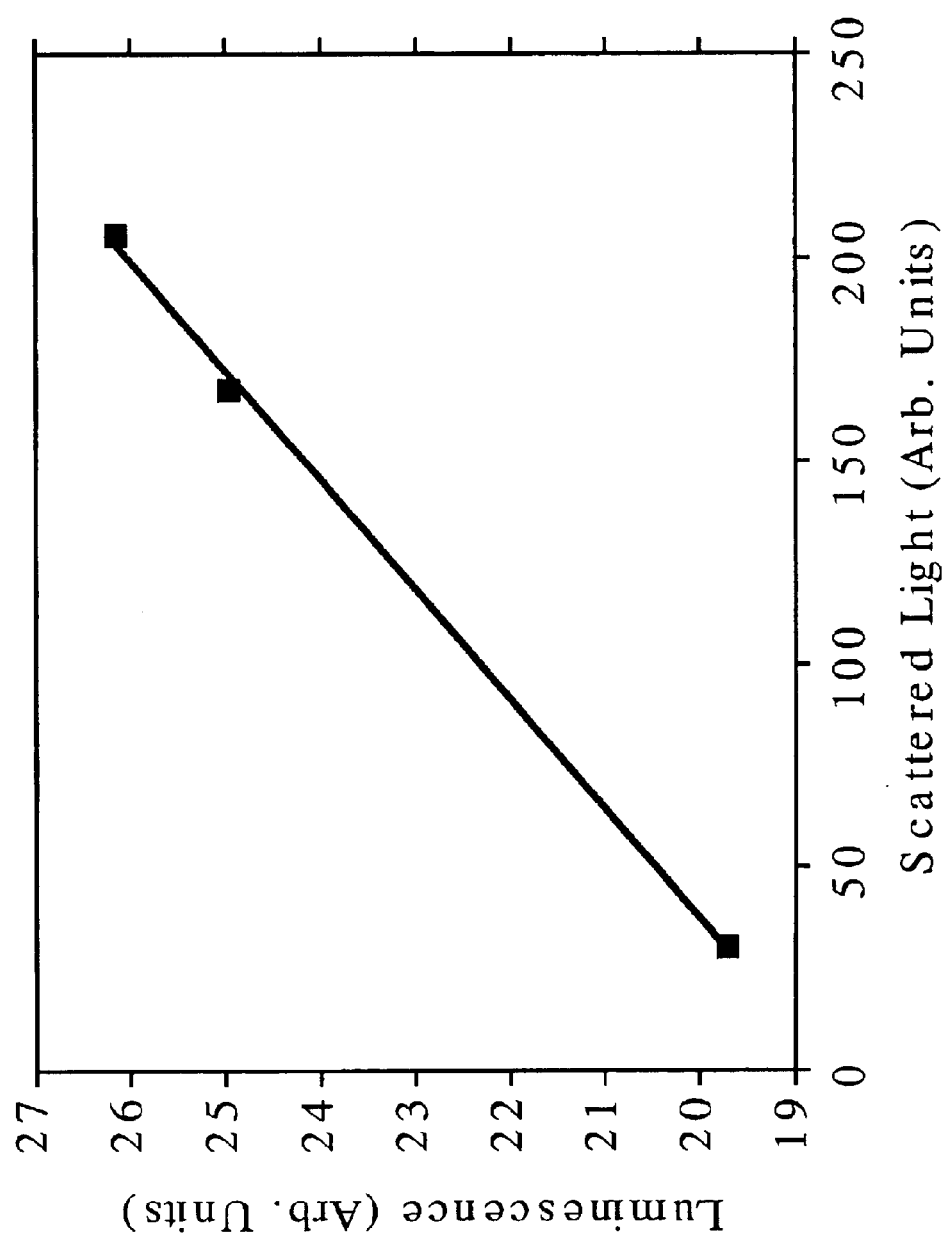
FIG. 11 is a plot illustrating the variation of intensity of luminescence from a coating as a function of resultant radiation from the coating obtained using a serial analysis method of measurement of distribution of resultant radiation and luminescence in an array of abraded coating regions.

FIG. 11 demonstrates the variation of intensity of luminescence from the coating as a function of scattered light induced by the sand blasting at different conditions (see example 2). The increase of luminescence is caused by the increased effective illumination area on the coating due to the greater scattering of excitation light from the coating and subsequent increase of luminescence intensity.

Although the present invention has been described with reference to preferred embodiments, other embodiments may achieve the same results. Variations in and modifications to the present invention will be apparent to those skilled in the art and the following claims are intended to cover all such equivalents.

What is claimed is:

1. A system for the optical interrogation of combinatorial arrays (12), comprising:
   a testing device (108) selected from the group consisting of an abrasion testing device, an elongation testing device, solvent exposure testing device, exposure to fluid testing device and a hydrolytic testing device to apply a varying test onto combinatorial array (12) to produce a combinatorial array of varying test results;
   a combinatorial array (12) having a surface (14) with a plurality of predefined regions, the plurality of predefined regions comprising one or more test result samples and reference regions resulting from testing in the testing device (108);
   a radiation source (16) operable, to expose each of the plurality of predefined regions of the combinatorial array (12) to incident radiation (20) of at least one selected wavelength and intensity;
   a detector (26) operable to measure resultant radiation (22) for each of the plurality of predefined regions of the combinatorial array (12); and
   a computer to functionally control the operation of the system and determine the relative performance of each of the plurality of predefined regions of the combinatorial array (12).

2. The system of claim 1, wherein the sample and one or more of the plurality of predefined reference regions is measured simultaneously.

3. The system of claim 1, wherein the surface (14) of the combinatorial array (12) is concave or convex.

4. The system of claim 1, wherein the combinatorial array (12) comprises a substrate with a deposited coating.

5. The system of claim 4, wherein the substrate exhibits inherent luminescence.

6. The system of claim 4, wherein the coating exhibits inherent luminescence.

7. The system of claim 4, wherein the coating comprises a transparent material or an opaque material.

8. The system of claim 4, wherein the coating comprises an organic material or an inorganic material.

9. The system of claim 4, wherein the substrate is comprised of a material selected from the group consisting of plastic, glass, metal, and composite material.

10. The system of claim 9, wherein the plastic comprises a film or plaque.

11. The system of claim 9, wherein the substrate comprises a transparent material or an opaque material.

12. The system of claim 1, wherein one or more of the plurality of predefined regions of the combinatorial array (12) further comprises at least one luminescent compound for reacting with the incident radiation.

13. The system of claim 12, wherein the luminescent compound is selected from the group consisting of a luminescent compound which is an organic dye, a luminescent compound which is an insoluble luminescent particle, a nanoparticle, a pigment, a luminescent compound whose emission properties are not affected by the microenvironment, and a luminescent compound whose emission properties are affected by the microenvironment.

14. The system of claim 1, further comprising a wavelength selection device (18) operable to receive incident radiation (20) and transmit incident radiation (20) having a selected range of wavelengths.

15. The system of claim 1, further comprising one or more filters for selectively absorbing incident radiation (20) of a selected range of wavelength.

16. The system of claim 1, wherein the wavelength of the radiation is from about 20 nm to about 25,000 nm.

17. The system of claim 1, further comprising an imaging device (34) operable to obtain an image of the resultant radiation (22) for each of the plurality of predefined region of the combinatorial array (12).

18. A method for optical interrogation, comprising the steps of:
providing a coated substrate;
applying a varying test onto the coated substrate to form an array of combinatorial varying test result regions, wherein the test is selected from the group consisting of an abrasion test, an elongation test, solvent exposure test, exposure to fluid test and a hydrolytic test;
exposing the array of varied test result regions to incident radiation (20) of at least one selected wavelength and intensity;
collecting resultant radiation (22) for the varied test regions of the combinatorial array (12);
and determining performance of varied test result regions according to respective resultant radiation.

19. The method of claim 18, wherein the step of applying tests forms test result regions and reference regions.

20. The method of claim 19, wherein the reference regions are substrate regions between result regions.

21. The method of claim 19, further comprising a step of measuring at least a portion of a reference substrate region end at least a portion of at least one result region simultaneously and determining performance using the portion of the reference substrate region as a reference.

22. The method of claim 18, wherein the substrate comprises a deposited coating.

23. The method of claim 18, wherein the substrate is either concave or convex.

24. The method of claim 22, wherein the substrate exhibits an inherent luminescence.

25. The method of claim 22, wherein the coating exhibits an inherent luminescence.

26. The method of claim 18, wherein one or more of the test result regions of the combinatorial array (12) has been physically exposed to at least one test selected from the group consisting of abrasion testing, exposure to temperature, elongation testing, exposure to at least one solvent for a predetermined period of time, exposure to at least one fluid for a predetermined period or time, and subjection to hydrolytic stability testing.

27. The method of claim 18, wherein one or more of the test result regions of the combinatorial array (12) further comprises at least one luminescent compound for reacting with the incident radiation.

28. The method of claim 27, wherein the luminescent compound is selected from the group consisting of a luminescent compound which is an organic dye, a luminescent compound which is an insoluble luminescent particle, nanoparticle, a pigment, a luminescent compound whose emission properties are not affected by the microenvironment, and a luminescent compound whose emission properties are affected by the microenvironment.

29. The method of claim 18, further comprising the step of selectively absorbing incident radiation of one or more predetermined wavelengths.

30. The method of claim 18, further comprising the step of obtaining an image of the resultant radiation (22) for each of the test result regions of the combinatorial array (12).

31. A method of testing and interrogating the results of the testing, comprising:
applying varying testing conditions across a substrate to form a pattern of varying test results;
exposing the pattern of varying test results to incident irradiation;
detecting radiation scattered from the pattern of varying test results; and
referencing detected scattered radiation to a position of a corresponding test result in the varying test result pattern to determine a varied testing condition that resulted in the scattered radiation.

32. The method of claim 31, comprising applying the varying testing conditions to form a pattern of test results with intermittent untested reference spacings and detecting radiation scattered from the pattern of test results with the spacings.

33. The method of claim 31, wherein the substrate comprises a deposited coating.

34. The method of claim 31, wherein the substrate has an inherent luminescence.

35. The method of claim 31, wherein the substrate comprises a deposited coating that has an inherent luminescence.

36. The method of claim 31, wherein tho substrate comprises a deposited coating that comprises a transparent material or an opaque material.

37. The method of claim 31, wherein the substrate comprises a deposited coating that comprises an organic material or an inorganic material.

38. The method of claim 31, wherein the substrate comprises a deposited coating that is a material selected from the group consisting of plastic, glass, metal, and composite material.

39. The method of claim 31 wherein the substrate comprises a deposited coating that comprise a film.

40. The method of claim 31, wherein the substrate comprises a deposited coating that comprises a transparent material or an opaque material.

41. The method of claim 31, wherein the varying resting conditions step comprises testing conditions of a test selected from the group consisting of abrasion testing, temperature exposure testing, elongation testing, solvent exposure testing; fluid exposure testing and hydrolytic stability testing.

42. The method of claim 31, wherein one or more of the test results of the pattern further comprises at least one luminescent compound for reacting with the incident radiation.

43. The method of claim 31, wherein one or more of the test results of the pattern further comprises at least one radiation reactive luminescent compound selected from the group consisting of an organic dye, a luminescent particle, a nanoparticle and a pigment.

44. The method of claim 31, wherein one or more of the test results of the pattern further comprise at least one radiation reactive luminescent compound selected from the group consisting of a luminescent compound with emission properties that are not affected by a microenvironment and a luminescent compound with emission properties that are affected by a microenvironment.

* * * * *